(12) United States Patent
Querol Garcia

(10) Patent No.: US 9,724,498 B2
(45) Date of Patent: Aug. 8, 2017

(54) THREE-LOBE DRAINAGE HOSE

(71) Applicant: Valeria Querol Garcia, Mexico City (MX)

(72) Inventor: Valeria Querol Garcia, Mexico City (MX)

(73) Assignee: Valeria Querol Garcia, Mexico City (MX)

( * ) Notice: Subject to any disclaimer, the term of this patent is extended or adjusted under 35 U.S.C. 154(b) by 675 days.

(21) Appl. No.: 13/919,859

(22) Filed: Jun. 17, 2013

(65) Prior Publication Data

US 2013/0281985 A1      Oct. 24, 2013

Related U.S. Application Data

(63) Continuation-in-part of application No. PCT/IB2010/055824, filed on Dec. 15, 2010.

(51) Int. Cl.
*A61M 1/00* (2006.01)
*A61M 27/00* (2006.01)
*A61M 25/00* (2006.01)

(52) U.S. Cl.
CPC ........ *A61M 27/00* (2013.01); *A61M 25/0032* (2013.01); *A61M 25/0017* (2013.01);
(Continued)

(58) Field of Classification Search
CPC .. A61M 1/008; A61M 27/00; A61M 25/0021; A61M 2025/004; A61M 25/0071; A61M 25/003; A61M 25/0032; A61M 2025/0034; A61M 2025/0031; A61M 2025/0037; A61M 25/0029; A61M 25/0043

See application file for complete search history.

(56) References Cited

U.S. PATENT DOCUMENTS

| | | | |
|---|---|---|---|
| 4,398,910 A * | 8/1983 | Blake | A61M 25/0071 604/266 |
| 5,378,230 A | 1/1995 | Mahurkar | |
| 5,451,206 A | 9/1995 | Young | |
| 5,486,159 A | 1/1996 | Mahurkar | |
| 6,478,789 B1 * | 11/2002 | Spehalski | A61M 27/00 604/264 |
| 6,485,481 B1 | 11/2002 | Pfeiffer | |
| 6,976,973 B1 * | 12/2005 | Ruddell | A61M 1/284 604/264 |
| 2004/0006311 A1 | 1/2004 | Shchervinsky | |
| 2004/0176745 A1 | 9/2004 | Ferguson | |
| 2005/0215949 A1 | 9/2005 | Bertolero et al. | |

(Continued)

FOREIGN PATENT DOCUMENTS

| | | |
|---|---|---|
| ES | 2329222 T3 | 11/2009 |
| GB | 2422410 A | 7/2006 |

(Continued)

OTHER PUBLICATIONS

PCT International Search Report for corresponding PCT Application No. PCT/IB2010/055824, dated Aug. 5, 2011.

(Continued)

*Primary Examiner* — Tatyana Zalukaeva
*Assistant Examiner* — Ariana Zimbouski
(74) *Attorney, Agent, or Firm* — Steven M. Koehler; Westman, Champlin & Koehler, P.A.

(57) ABSTRACT

A drainage system includes a drainage tube, a tubular coupling, and a drainage hose. The drainage tube defines an inner passage and terminating in a first drainage end and a second drainage end. The tubular coupling has a first thickness that runs throughout the coupling and forms a passage and a stop determined by a second thickness. The drainage hose is formed by a profile which runs along a length of the drainage hose and terminates in a first drainage end and a second drainage end.

18 Claims, 14 Drawing Sheets

(52) U.S. Cl.
CPC ............... *A61M 2025/0004* (2013.01); *A61M 2025/0059* (2013.01)

(56) References Cited

U.S. PATENT DOCUMENTS

| | | | |
|---|---|---|---|
| 2007/0117010 A1* | 5/2007 | Shang | A61M 1/16 429/163 |
| 2008/0319419 A1 | 12/2008 | Kato et al. | |
| 2010/0049147 A1 | 2/2010 | Tanikawa et al. | |

FOREIGN PATENT DOCUMENTS

| | | | |
|---|---|---|---|
| JP | 2007202901 | A | 8/2007 |
| MX | 2008014160 | A | 11/2008 |
| WO | 99/07301 | | 2/1999 |
| WO | 0136021 | A1 | 5/2001 |
| WO | 0230489 | A2 | 4/2002 |
| WO | 2007/082157 | A2 | 7/2007 |
| WO | 2009120871 | A2 | 10/2009 |
| WO | 2010060227 | A1 | 6/2010 |

OTHER PUBLICATIONS

PCT International Written Opinion for corresponding PCT Application No. PCT/IB2010/055824, dated Aug. 5, 2011.

* cited by examiner

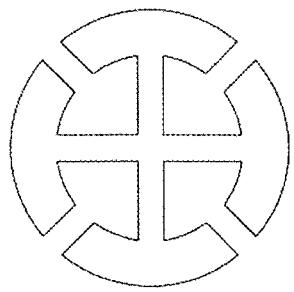 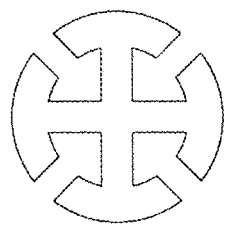 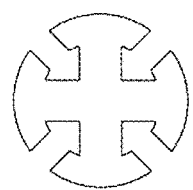 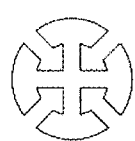
FIG. 5A   FIG.5B   FIG.5C   FIG.5D
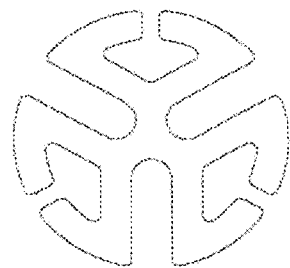 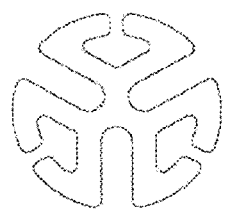 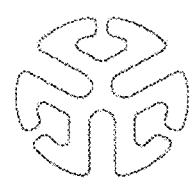 
FIG. 6A   FIG.6B   FIG.6C   FIG.6D

THREE-LOBE DRAINAGE HOSE

CROSS REFERENCE TO RELATED APPLICATION

This is a continuation-in-part of International Application No. PCT/IB2010/055824, filed Dec. 15, 2010, as published as WO 2012/080783, which is incorporated by reference in its entirety.

FIELD

Aspects of the present invention relate to the industry for manufacturing and commercializing medical instruments. Particularly, aspects of the present invention are addressed to a three-lobe hose for use into a medical, surgical, and/or post-surgical drainage system.

BACKGROUND

The prior art includes drainage hoses or drain for medical use, such as prophylactic, surgical, or post-operative use. Within this wide range of medical drainage hoses, there are usually two types: a closed-type and an open-type.

If a drain hose has one or more internal channels, that can cause occlusion or blockage due to the fluid being extracted, such as, for example, blood coagulation or deposition of other type of fluids. In some cases it is desirable that a drain hose is formed by more than one channel or canal. Therefore, in case of occlusion occurrence, the other canals may maintain fluid communication with the drainage area. Likewise, closed-type suction drainage systems are not exclusively limited for extracting fluids. At the same time, said systems may serve for introducing some kind of solution into the drainage area. For example, for saline spraying or flushing, it is often desired to have more than one channel or canal. A drain with external channels can also represent a risk for clogging or blocking, meaning that the light beam is occluded, but less likely than in the first ones.

Moreover, during usage, these drainage hoses are subjected to a variety of inner pressures inside the body, such as the oozing fluid pressure or the pressure resulting from the masses of skin or other tissues where the drain passes through. Based on the above, it is desired that a drain or drainage hose be provided with a strong and resistant structure for use in the medical field. To further illustrate this point, in case that a drainage hose collapses inside the body, it will block the fluid drainage path. Likewise, it is also desired to prevent the collapse of the structure or occlusion of a suction drainage system drainage hose (which can occur due to the suction system pressure internally "sucking" the hose).

Furthermore, another desirable feature in a drain refers to the extracting capacity of the fluids in the lowest possible time, so that the drain stay as short as possible. Thus, it is desired that a drain has a configuration that optimizes the flowing surface.

When finalizing usage, the drain is extracted from the patient's body. During the extraction procedure, the drain must be folded or rotated in a clockwise direction and backwards over its axis a few times. Therefore, the drain can have a symmetrical shape that facilitates the extraction procedure.

As has been mentioned in the preceding paragraphs, all of the above features should be present in the drainage hoses manufactured nowadays. However, there is prior art indicating that not every drain meets with all the desirable features. The following are some of these documents and its disadvantages currently.

The prior art describes various drainage systems and catheters. For example, patent applications WO2010060227, GB2422410, and MX2008014160 describe drainage hoses with more than one internal canal. Any of these inventions have the risk of fluid flow obstruction, but in addition, the asymmetrical shape of the outer hinders the extraction procedure described above.

Moreover, the US Patent Application No. US20080319419 describes a drain with two internal canals that run symmetrically arranged. Additionally, the exterior of this drain is circular so it facilitates extraction operations. However, its tubular configuration, where both canals are separated by a partition, does not provide this drain with sufficient structural strength to prevent collapse.

The same occurs for other drainage hoses or catheters which run inside more than two internal canals, as disclosed in the international application publication no. WO2009120871, US application publication no. US20100049147, Japanese patent application no. JP2007202901, as well as U.S. Pat. Nos. 6,485,481, 5,486, 159, 5,451,206, and 5,378,230. While all these drainage hoses have various internal canals, and a circular outer shape that facilitates the removal thereof, the configurations of these structures are not optimal for preventing collapse or providing adequate flow of the extracting fluid. Moreover, for being a closed-type drainage hoses, all of them have a high risk of inner clogging/obstruction during usage. The same disadvantages are also true for US patent application no. US20050215949 whose external shape is slightly elliptical.

There are also a variety of drainage systems having drain hoses with canals and outer grooves, which minimize the risk of clogging of the canal. However, some of these hose designs do not allow flow optimization and do not always have an adequate structural strength to support compression due to the surrounding organs and tissue.

Also, there are some mixed drainage hoses that have both external canals and internal conduits for fluid communication. An example of this type of drain or catheter is described in the international publication no. WO2002/030489 for peritoneal dialysis usage, where some embodiments have both external canals and internal conduits. However, the configuration of this type of catheter/drain does not allow flow optimization and does not provide structural strength to the catheter/drain.

Some relevant art may be found in the international publications nos. WO2001/036021 and WO2007/082157, as well as the catheter/drain commonly known as Blake, a surgical and medical industry standard, originally described in U.S. Pat. No. 4,398,910.

International application WO2001/036021 describes a drain that has a symmetrical configuration of multiple ducts and lumen. In the preferred first embodiment, the transversal drain configuration is a cross shape comprising four ducts and four lumens, conforming a mixed system wherein the ducts have outer fluid communication and the lumens have inner fluid communication. The disadvantage of this configuration is that the inner lumens have the same risk of clogging than the closed-type drain described above. Moreover, the '021 application also illustrates a configuration where some portals maintain fluid communication between ducts and lumens. This causes even more blockage risk areas, such as the circumferential edges of the lumens. Additionally, the formation of these portals in the lumens walls can significantly weaken the structural strength of the drain, increasing the collapse risk. Also, the cross-shaped configuration does not always provide the best configuration before radial forces; a triangular configuration works better for such purposes.

International application WO2007/082157 describes a triangular-configuration drain for medical applications and uses. The advantages of this drain are a configuration having three lumens or drainage canals, and outer walls curved in a substantially circular manner to avoid difficulties during drain removal from a patient. However, due to the fact that the drain circumferential walls extend in clockwise direction, there is a high risk that could negatively affect the drain removal actions from the patient, wherein said drain is rotated. That is, if during the removal action the rotation is taken in the wrong direction, the patient may experience pain and complications. In addition, the drain core comprises an internal passage with the above-described high clogging or occlusion risks.

Finally, U.S. Pat. No. 4,398,910 corresponds to the catheter known in the medical field as "Blake." This catheter corresponds to a drain conformed by four symmetrical distributed lumens. While it may be the case that the Blake drain can drain fluids properly with low occlusion risk of the light beam and good structural strength, the effective flow area, as well as structural strength, of the Blake catheter can be improved. As mentioned, the Blake drain is now commonly used in the medical-surgical industry. However, the disadvantages that this design keeps with respect to aspects of the present invention will be demonstrated later in the comparative analysis that accompanied this description.

Therefore, a new drain design that overcomes the above-mentioned disadvantages of the prior art is desired.

SUMMARY

A drainage system includes a drainage tube, a tubular coupling, and a drainage hose. The drainage tube defines an inner passage and terminating in a first drainage end and a second drainage end. The tubular coupling has a first thickness that runs throughout the coupling and forms a passage and a stop determined by a second thickness. The drainage hose is formed by a profile which runs along a length of the drainage hose and terminates in a first drainage end and a second drainage end.

BRIEF DESCRIPTION OF THE DRAWINGS

A more complete understanding of the drainage hose described herein may be derived by referring to the following accompanying figures:

FIG. 5A is a view of a Blake drainage hose known in the prior art of 24 FR or French (8 mm).

FIG. 5B is a view of a Blake drainage hose known in the prior art of 19 FR or French (6.33 mm).

FIG. 5C is a view of a Blake drainage hose known in the prior art of 15 FR or French (5 mm).

FIG. 5D is a view of a Blake drainage hose known in the prior art of 10 FR or French (3.33 mm).

FIG. 6A is a view of the drainage hose of 24 FR or French (8 mm).

FIG. 6B is a view of the drainage hose of 19 FR or French (6.33 mm).

FIG. 6C is a view of the drainage hose of 15 FR or French (5 mm).

FIG. 6D is a view of the drainage hose of 10 FR or French (3.33 mm).

DETAILED DESCRIPTION OF ILLUSTRATIVE EMBODIMENTS

Without limitation some objectives of the present invention are provided below. A first objective is to provide a drainage system comprising a drainage hose with several external canals along its trajectory.

A second objective of the present invention is to provide a drainage hose is formed from a configuration that provides structural strength that can resist the compression of organs and tissues, maintaining thus the constant shape design obtaining a better performance in the fluids extraction.

Another object of the present invention is to optimize the drainage fluid flow, thereby improving a patient's recovery time.

Moreover, another object of the present invention is to avoid the risk of blockage or "sealing" of the drain caused by deposition of the extracted fluids.

Finally, another objective is that the hose maintain outer symmetry preventing pain and complications for the patient when removing the drain.

In this regard, there is a need for a drainage hose with a triangular-type symmetrical configuration which provides structural strength, optimizes the drained fluid flow, avoids the drain blocking risk due to deposition of extracted fluids, and prevents complications for the patient when removing the drain from the patient.

Figure 1:
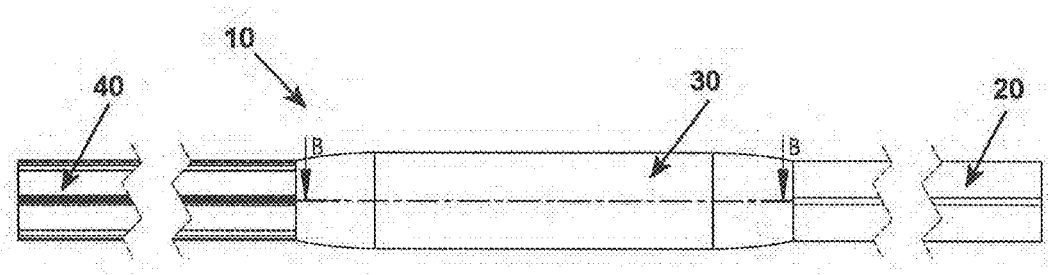
FIG. 1 is a side view of the drainage system and its components.
Figure 2A:
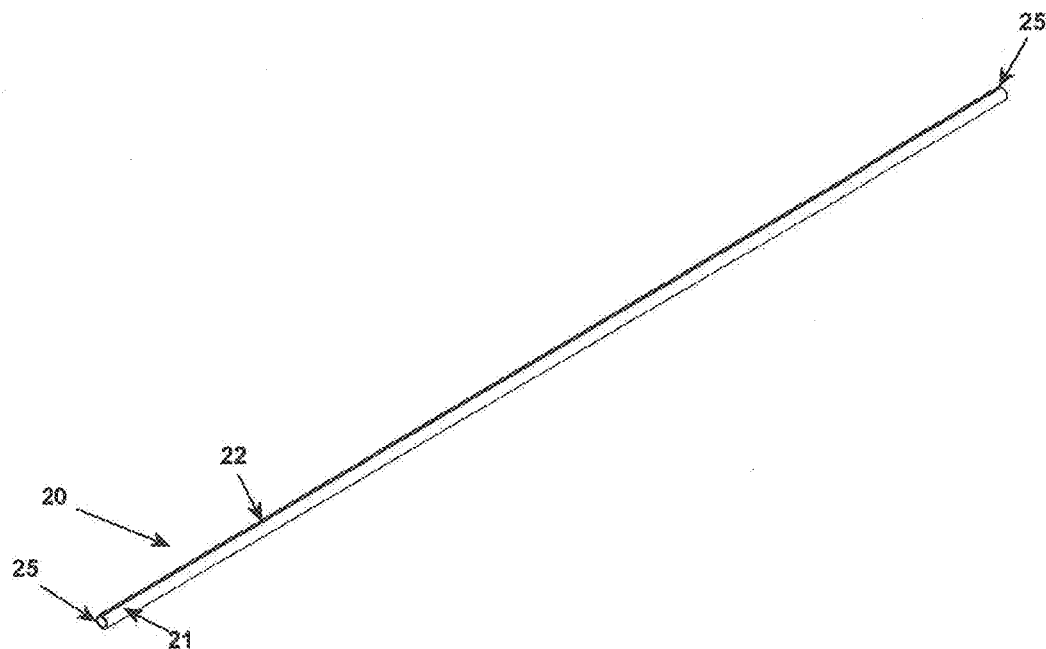
FIG. 2A is a perspective view of the drainage tube that conforms the drainage system.
Figure 2B:
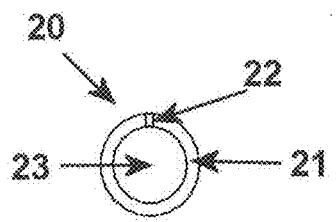
FIG. 2B is a cross-sectional view of the drainage tube that conforms the drainage system.

Embodiments of the present invention relate to a drainage system. As shown in FIG. 1, a drainage system (10) is made up of three main components: a drainage tube (20), a coupling (30), and a drainage hose (40). Features, function and coupling method of these components are described in greater detail below:

FIGS. 2A and 2B show the drainage tube (20), which is a tube having a constant outer and inner diameter that conforms to a wall thickness (21). The inner diameter defines a passage (23) (shown in FIG. 2B) where fluids extracted by the drainage system (10) are circulated. The drainage tube (20) terminates in a first drainage end and a second drainage end (25). In a preferred embodiment, the tube (20) can measure about 675 mm in length, 8 mm in outer diameter, and 6 mm in inner diameter in a size 24 FR. However, these dimensions and thicknesses may vary in different ways for adapting to the required medical use. For example, different sizes of the catheter French scale can include: 3, 4, 5, 6, 7, 8, 9, 10, 11, 12, 13, 14, 15, 16, 17, 18, 19, 20, 22, 26, 28, 30, 32 or 34, among others.

Additionally, the drainage tube (20) has a radiopaque line (22) extending longitudinally in the drainage tube (20). The radiopaque line (22) can be identified with the naked eye, because unlike the rest of the system, it is not transparent. Said line is used to identify the drain position when making x-rays. Preferably, said radiopaque line (22) is achieved by combining silicone with barium through known methods. In one embodiment not illustrated, the drainage tube can include barium or any other radiopaque material, combined together entirely with the drainage tube.

Figure 3A:
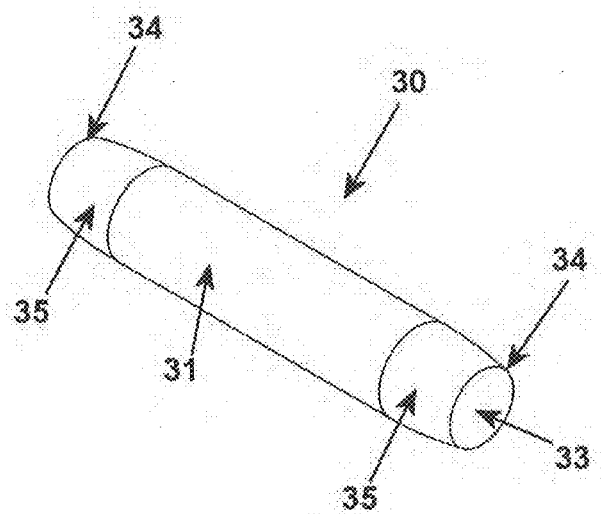
FIG. 3A is a perspective view of the coupling conforming the drainage system.
Figure 3B:
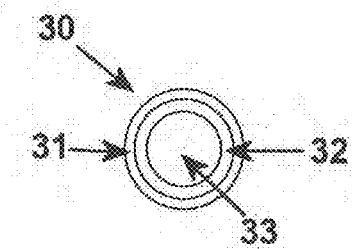
FIG. 3B is a cross-sectional view of the coupling conforming the drainage system.
Figure 3C:
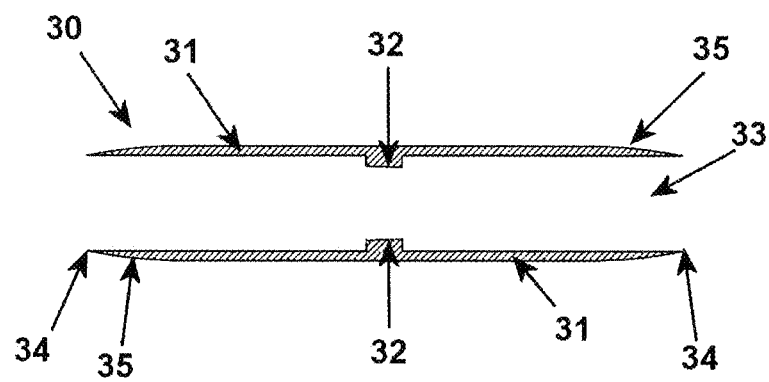
FIG. 3C is a longitudinal sectional view in lines B-B of FIG. 1 of the coupling conforming the drainage system.

FIGS. 3A, 3B and 3C illustrate different views of the coupling (30) which corresponds to a substantially cylindrical tubular structure. The coupling (30) has a first thickness (31) that runs along the entire piece forming a passage (33) in the tubular structure. Also, the coupling (30) has a stop (32) that is determined by a second thickness. The first thickness is less than the second thickness. Preferably, the stop (32) is located in the longitudinal middle of the coupling (30). Said stop can be plane or can have another shape, such as conic, among others. Additionally, in each of a first coupling end and a second coupling end (34) of the coupling (30) there is a outer reduction of material in the first thickness (31), which forms a curving or bevel (35). In a preferred embodiment, the coupling (30) can measure about 50 mm in length, 9.2 mm in outer diameter, and 8 mm in inner diameter at the first thickness, as well as 6 mm in diameter and 1 mm in thickness in the area of the stop (32).

Figure 4A:
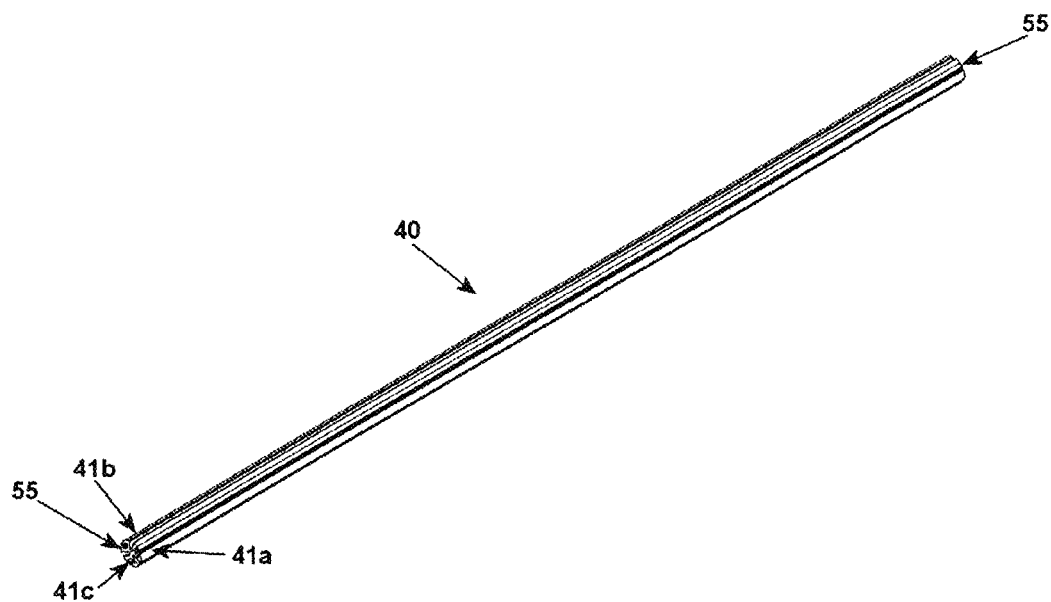
FIG. 4A is a perspective view of the drainage hose that conforms the essential part of the drainage system.
Figure 4B:
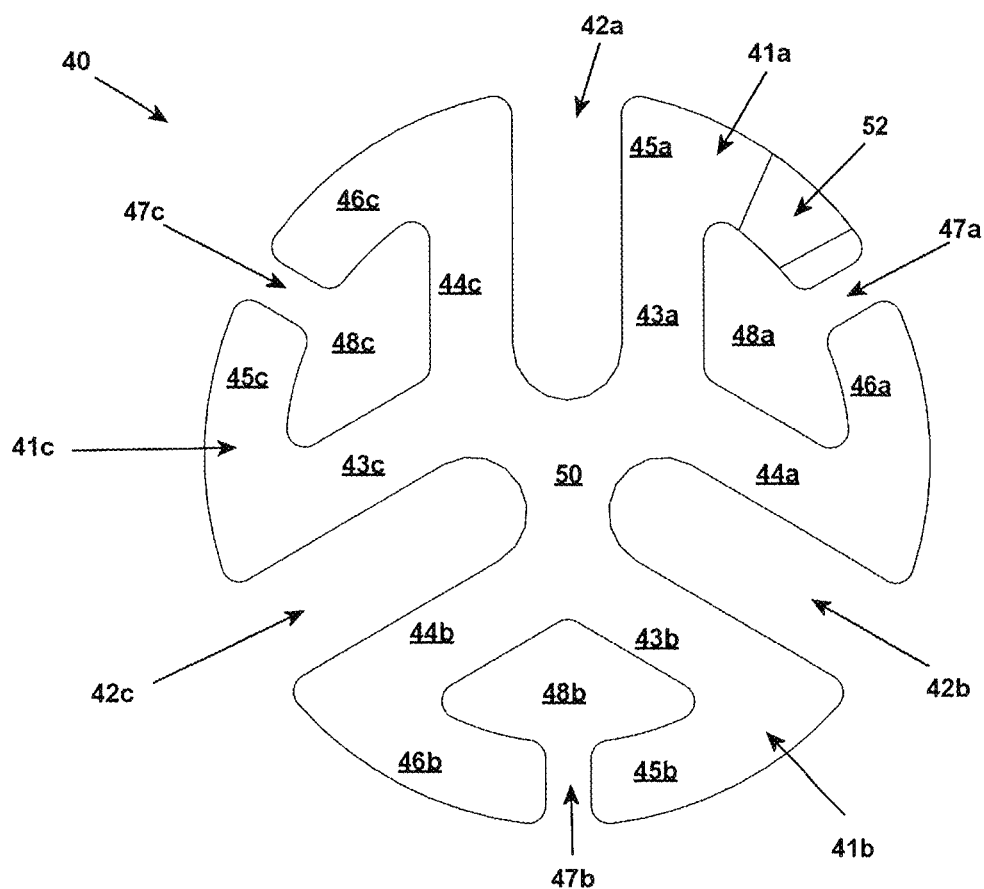
FIG. 4B is a cross-sectional view of the drainage hose that conforms the essential part of the drainage.

FIGS. 4A and 4B illustrate the drainage hose (40). Drainage hose (40) is formed by a lobed profile that runs along the entire length thereof. FIG. 4B shows a cross-section of the drainage hose (40) wherein there are three symmetrical lobes (41a), (41b), (41c). Lobes (41a), (41b), and (41c) are delimited therebetween by three dividing channels (42a), (42b), and (42c). Each lobe (41a), (41b), (41c) is made up of two radial straight walls (43a, 44a), (43b, 44b), (43c, 44c) at the center (50) of the hose structure and two circumferential curved walls (45a, 46a), (45b, 46b), (45c, 46c) in opposite directions at the periphery of the hose. As shown in FIG. 4B, the angular distance of the two radial straight walls is 120 degrees. Each radial straight wall is connected to a circumferential curved wall. Additionally, circumferential curved walls (45a, 46a), (45b, 46b), (45c, 46c) have opposite directions, however they do not bind together due to spaces (47a), (47b), (47c) formed between the two walls on the circumference of each lobe (41a), (41b), (41c), respectively. Radial straight walls (43a, 44a), (43b, 44b), (43c, 44c) and circumferential curved walls (45a, 46a), (45b, 46b), (45c, 46c) define a lumen (48a)(48b), (48c), while the other side of radial straight walls (43a, 44a), (43b, 44b), (43c, 44c) define the dividing channels (42a), (42b), (42c). As shown in FIG. 4A, the drainage hose (40) terminates in a first drainage end and a second drainage end (55). As shown in FIG. 4B, all vertices and edges formed between all these components of the drainage hose (40) have been rounded to reduce the spaces where blockage or clogging could easily start to form. In a preferred embodiment, the hose (40) can measure about 325 mm in length and 8 mm in outer diameter, the dividing channels (42a), (42b), (42c) can measure about 1.2 mm in width and the spaces (47a), (47b), (47c) can measure about 0.5 mm.

In the same way as the drainage tube (20), the drainage hose (40) has a radiopaque line (52) extending longitudinally in the drainage hose (40). Also, the radiopaque line (52) can be identified with the naked eye, because unlike the rest of the system, it is not transparent. Similarly, this line is used to identify the drain position when making x-rays. Preferably, said radiopaque line (52) is achieved by combining silicone with barium through known methods.

In addition, in one embodiment, the drainage hose (40) can include a plurality of perforations (not shown) of different shapes, to provide fluid communication with the interior of the lumens (48a), (48b), (48c).

The components of the drainage system (10) are assembled in a manner known in the prior art. The drainage tube (20) is inserted into one end (34) of the coupling (30) along a first region of the passage (33) running along the first thickness (31) until the end (25) of the drainage tube (20) abuts the stop (32). Similarly, the drainage hose (40) is inserted into the other end (34) of the coupling (30) along a second region of the passage (33) running along the first thickness (31) until the end (55) of the drainage hose (40) abuts the stop (32). In this way, passages (23) and (33) are in fluid communication with dividing channels (42a), (42b), (42c) and lobular lumen channels (48a), (48b), (48c), thus conforming the drainage system (10).

Embodiments of the present invention provide a larger flow area per cross-sectional area. In this regard, FIGS. 5A to 5D illustrate different cross-sections of the Blake drainage hose, while FIGS. 6A to 6D show equivalent cross-sections in accordance with embodiments of the present invention. Calculations were made on the construction area, the open area, and the percentage area of the circle that circumscribes the cross-section of the drainage hoses, as well as the comparison percentage of the drainage hose (40) versus the Blake drainage hose. These calculations are shown in the following table:

TABLE 1

| Hose size | Construction area (mm²) | Free flow area (mm²) | Free flow area % | Comparison with Blake equivalent % |
|---|---|---|---|---|
| Blake 24FR | 30.966 | 19.299 | 38.39% | — |
| Blake 19FR | 19.319 | 9.906 | 33.90% | — |
| Blake 15FR | 14.527 | 5.108 | 26.01% | — |
| Blake 10FR | 6.579 | 3.042 | 31.62% | — |
| Hose (40) 24FR | 29.930 | 20.336 | 40.46% | 5.40% more |
| Hose (40) 19FR | 17.462 | 11.763 | 40.25% | 18.70% more |
| Hose (40) 15FR | 11.794 | 7.841 | 39.93% | 53.50% more |
| Hose (40) 10FR | 5.671 | 3.950 | 41.06% | 29.90% more |

Based on the above, it is concluded that the drainage hose (40) has a free flow area between 39% to 42% of the area of the outer diameter that circumscribes the cross-section. Also, it is clear that this ratio remains optimized after dimensional change for a hose varying its outer diameter. Moreover, the percentage of free flow area is higher when compared with the Blake-type drainage hoses in equivalent thickness. Even more, the ratio of the free flow area is maintained within the mentioned range for the present invention, whereas the Blake hoses is variable, which results in a disadvantage to the standardization of the functional characteristics of the product.

Figure 7A:
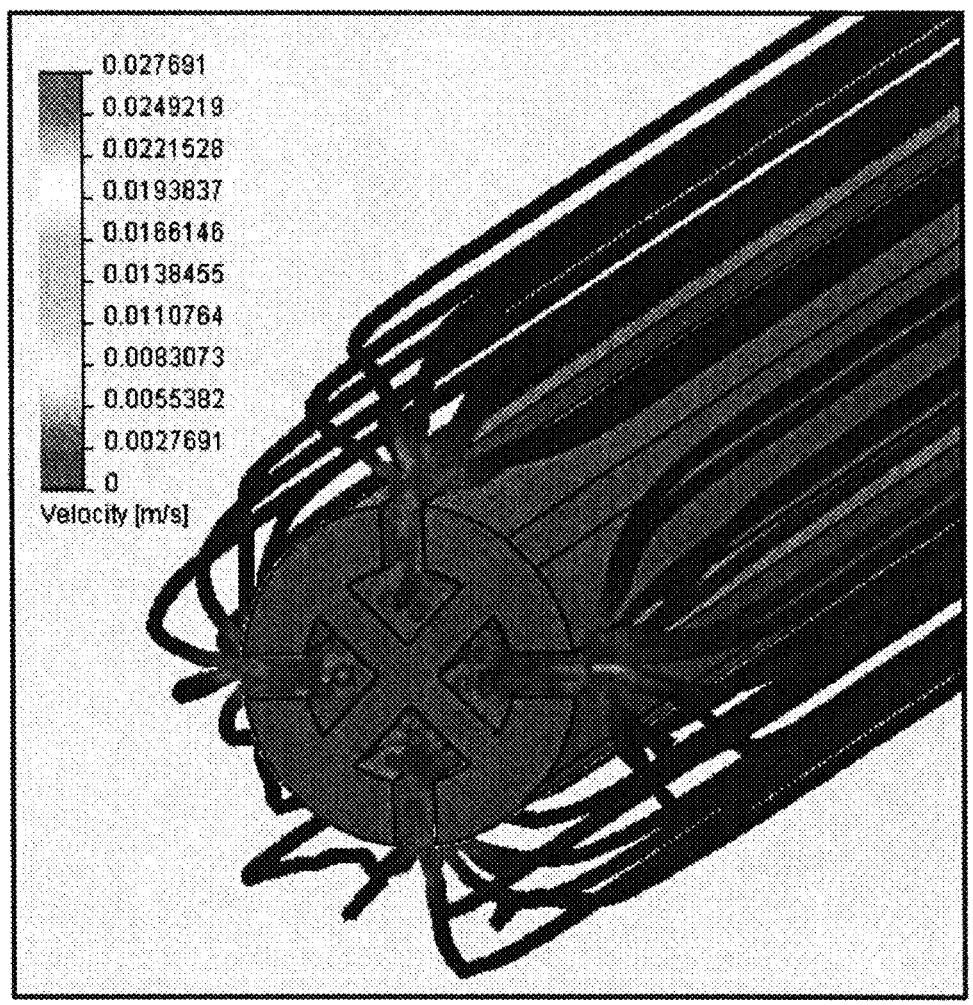
FIG. 7A is a view of a finite element flow analysis on a Blake drainage hose known in the prior art of 24 FR or French (8 mm).
Figure 7B:
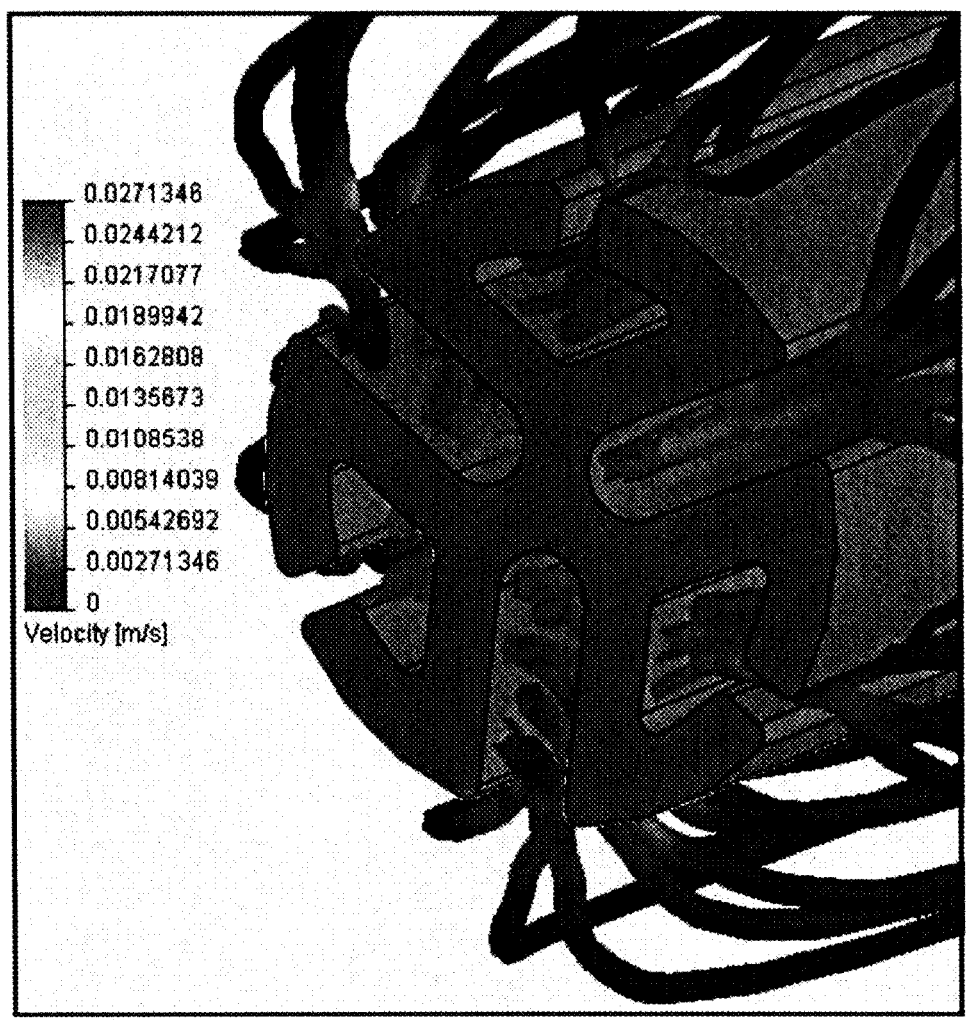
FIG. 7B is a view of a finite element flow analysis on the drainage hose of the present invention of 24 FR or French (8 mm).

First, the drainage hose (40) provides various external channels (42a), (42b), (42c), (48a), (48b), (48c) along its path, allowing an adequate flow of the drainage fluid. Said channels opened to the outside significantly reduce the risks of occlusion or blockage of the drainage system (10) caused by deposition of the extracted fluids. FIGS. 7A and 7B show the results of a first comparative analysis of the drainage hose of the present invention and the Blake-type drainage hose.

Analysis 1: Finite Element Flow.

The first analysis considered the drainage hoses illustrated in FIGS. 5A and 6A, which were analyzed by the finite element method to obtain the characteristics shown by these drainage hoses when a fluid flows through them. This type of simulation took into consideration a length of 30 cm, as it is the maximum length of production for this device. Furthermore, the analysis contemplated a fluid density of 1.052 to 1.063 (kg/m³), fluid viscosity of $3.5 \times 10^{-3} = (0.0035$ Pa), fluid thermal conductivity of $0.492 \pm 0.009$ W/m-K, and fluid specific heat of 3500 J/kg-k. Fluid environments were performed in a space of 300 mm length and 8 mm radius. The imaginary space is an ideal environment in which the drain is placed to simulate the maximum speed in which fluids enter the drainage channels. Nonetheless, the analysis refers to the maximum momentum, which means that it is not a function of time.

This analysis allowed determining the maximum speed of the fluid in an open environment, where were contemplated both hoses aspects regarding how these collect the fluid. Determinant factors to solve the system were: a 310 K temperature corresponding to the internal temperature of the organism, which is the optimum operational temperature; a 2000 Pa pressure corresponding to the fluid extraction pressure of a Pleurovac equipment; and a flow determined by several experiments conducted in the Department of Experimental Surgery within the National Institute of Medical Sciences and Nutrition Salvador Zubirán in Mexico.

To perform each of these analyses, there was a defined space calculation as environment, as well as the vacuum space of the drainage hoses, in order to have a solid that represents that three-dimensional space, corresponding to the volume where it is desired to analyze the fluid behavior. From such space, there was performed a mesh with diverse criteria to analyze both the space and the hose, as two different objects with constant and independent cross-sections. This method was implemented to vary the mesh repetitions in two dimensions, along the model for forming first order hexas, as these items are the most recommended for a good quality mesh allowing analyzing the convergence of the desired value and minimizing error. The analyses consider the fluid as a laminar flow in the axial direction along its length.

As shown in FIGS. 7A and 7B, speed increases in accordance with the difference of the free cross-section areas where fluids flow. From these simulations there was obtained a fluid speed of 0.027 m/s in both hoses. That is, the efficiency of the fluid flow is similar in both designs.

In the same way, the configuration of the three-lobe structure drainage hose (40) provides a support based on one of the most stable configuration of the nature, such as a triangle. In the drainage hose (40), the basic support is given by the radial straight walls (43a, 44a), (43b, 44b), (43c, 44c). This configuration provides the structural strength in the radial direction of the hose (40), as the pressures of the organs or tissues to which the piece will be subject come in such direction. Therefore, such three-lobe configuration is suitable and resistant for the medical usages of the piece, as shown in the finite element analysis shown in FIGS. 8A and 8B, which will be explained as follows.

Analysis 2: Structural Finite Element

Figure 8A:
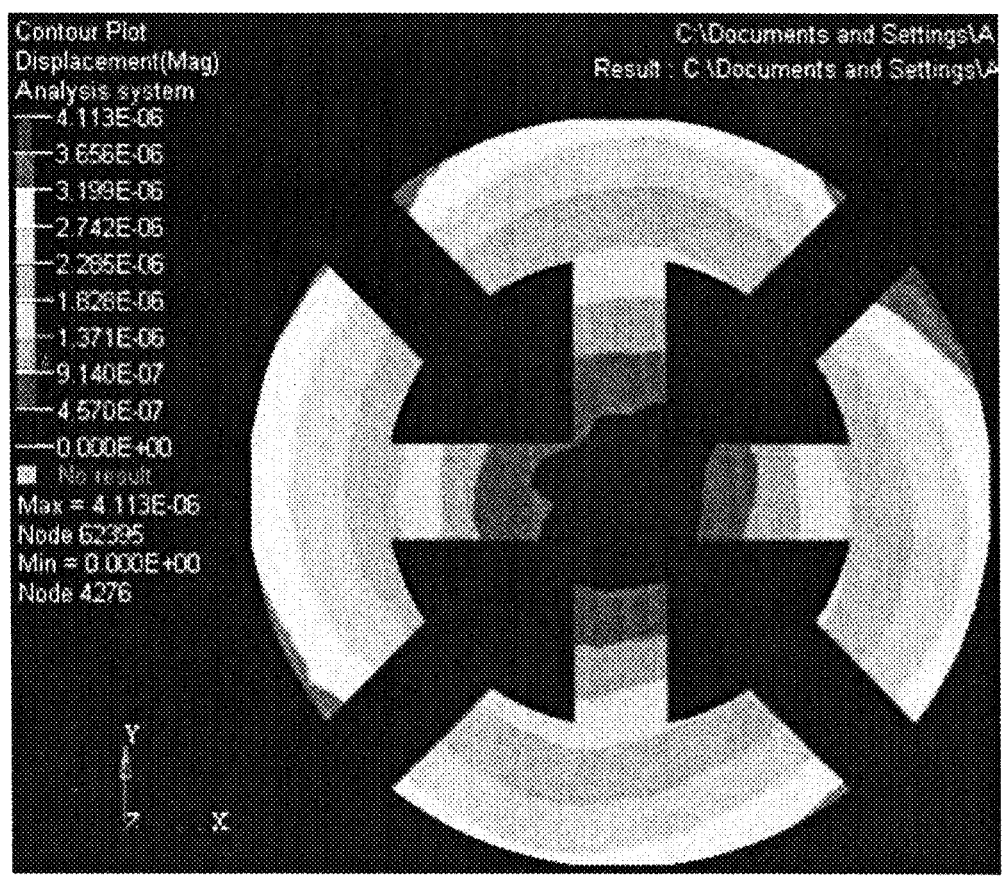
FIG. 8A is a view of a finite element stain flow structural analysis in a Blake drainage hose known in the prior art of 24 FR or French (8 mm).
Figure 8B:
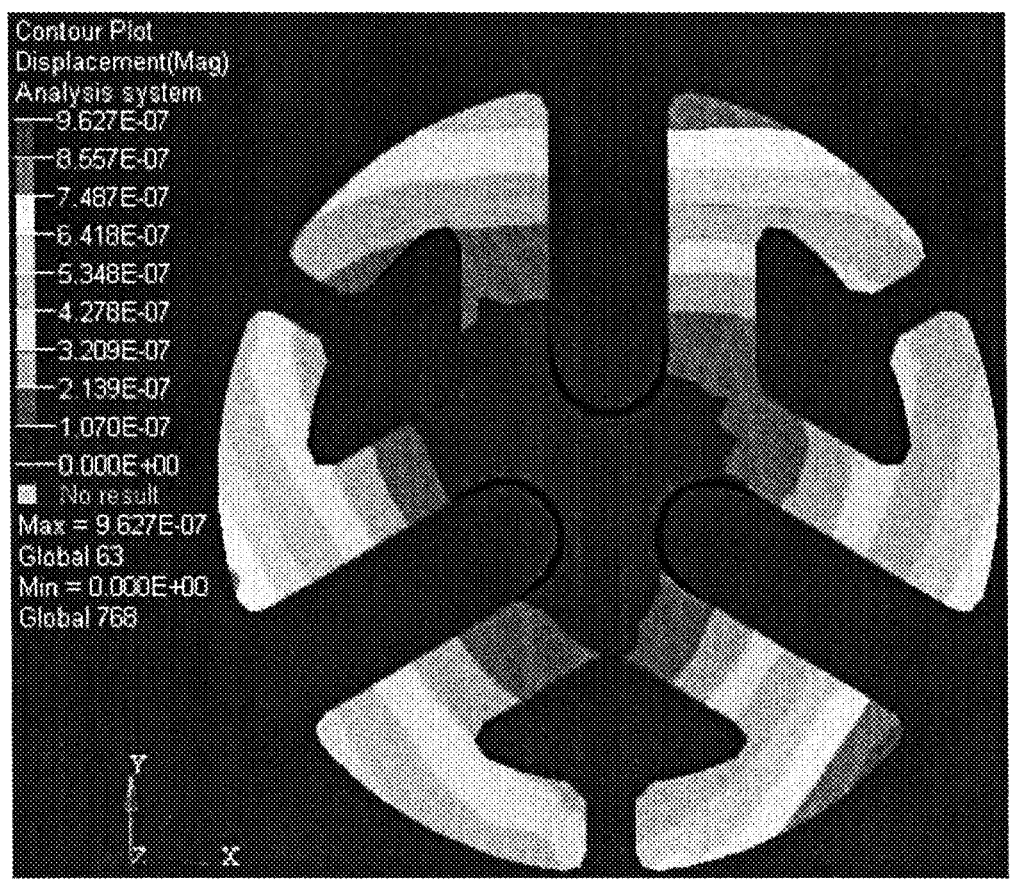
FIG. 8B is a view of a finite element stain flow structural analysis in the drainage hose of the present invention of 24 FR or French (8 mm).
Figure 9A:
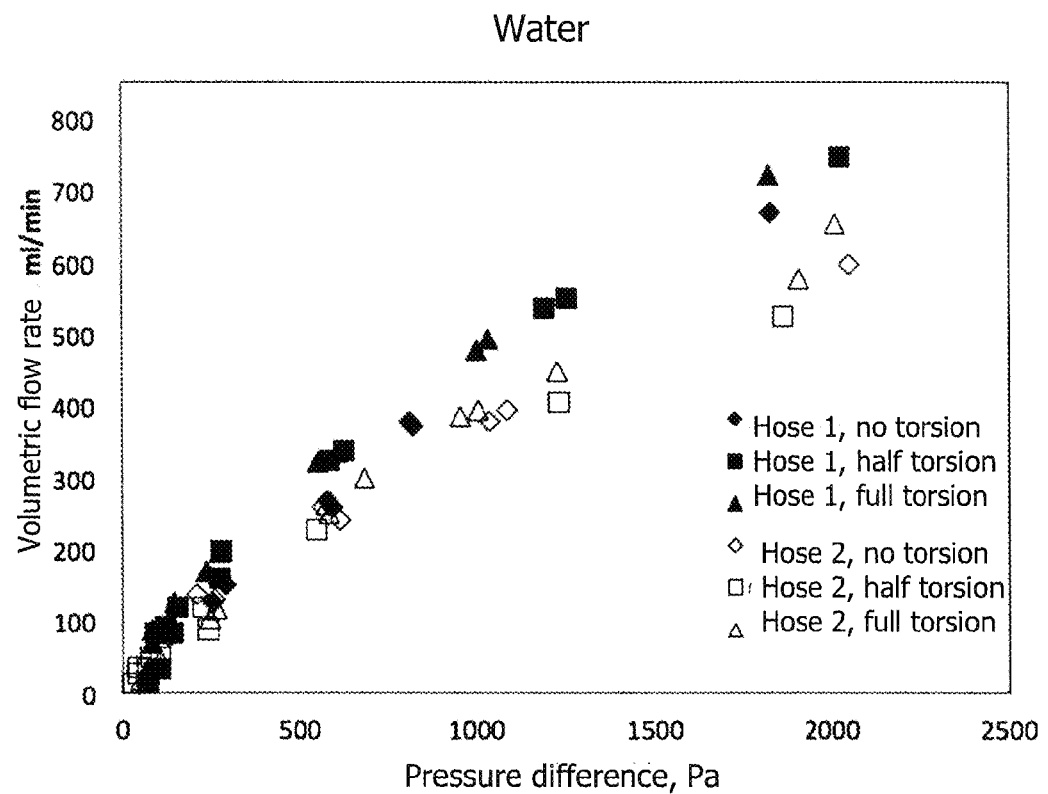
FIG. 9A is a volumetric flow chart of the drainage hose of the present invention and a hose of the prior art, using water as a fluid.
Figure 9B:
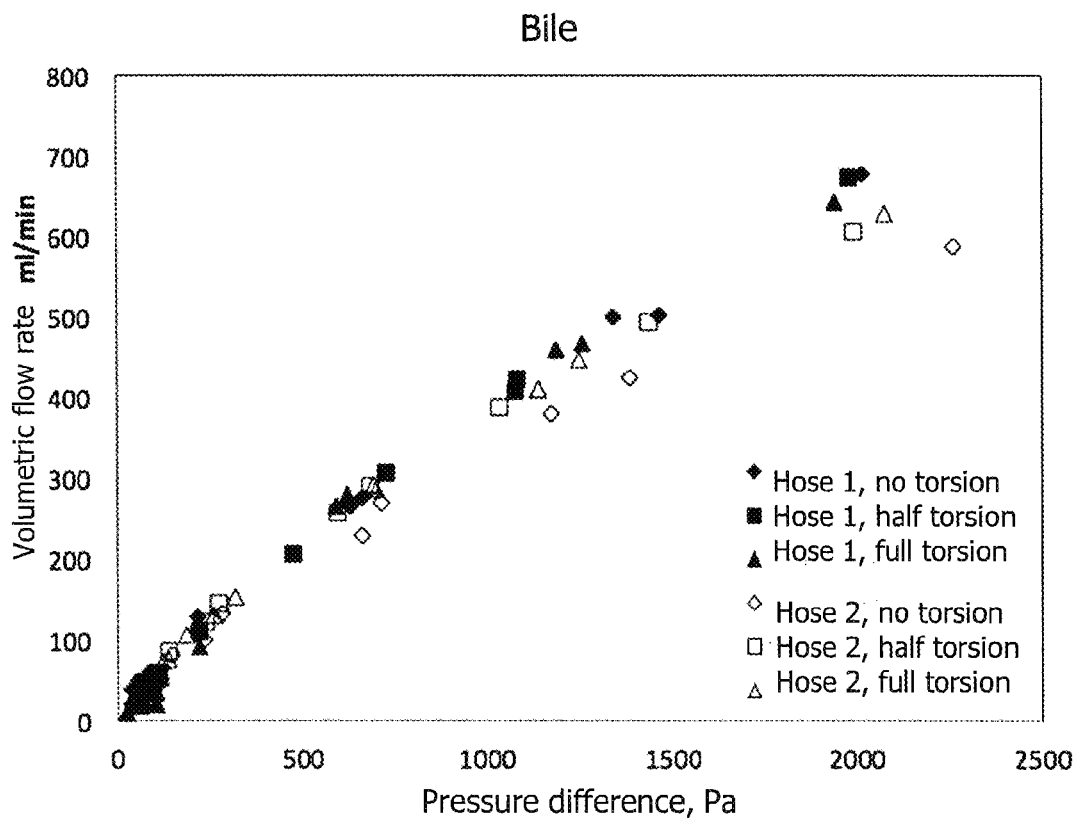
FIG. 9B is a volumetric flow chart of the drainage hose of the present invention and a hose of the prior art, using as fluid a substance having the same density and physical properties of bile.
Figure 9C:
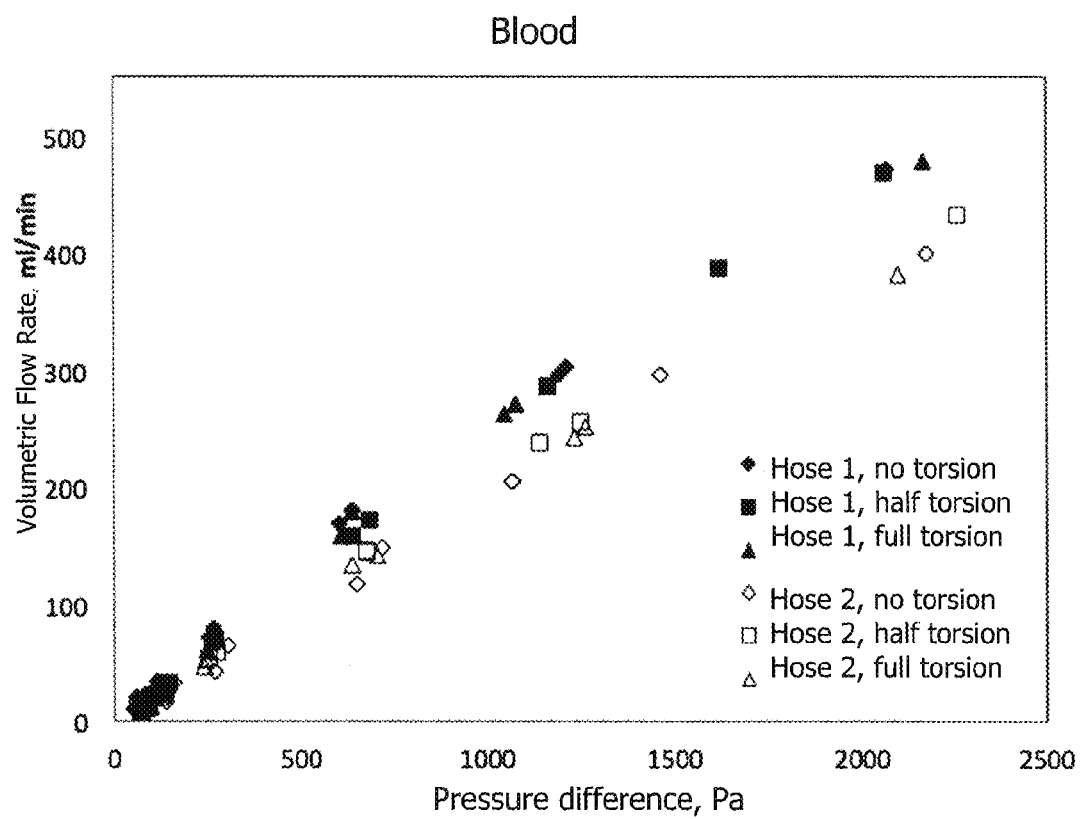
FIG. 9C is a volumetric flow chart of the drainage hose of the present invention and a hose of the prior art, using as fluid a substance having the same density and physical properties of blood.
Figure 9D:
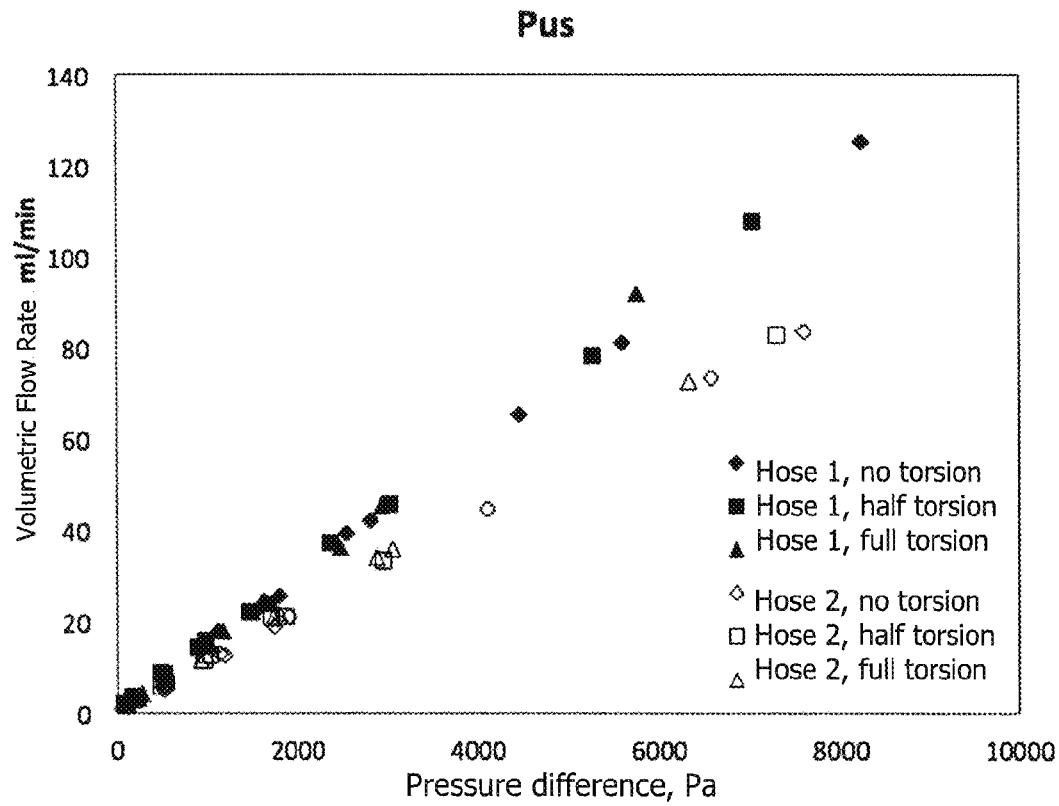
FIG. 9D is a volumetric flow chart of the drainage hose of the present invention and a hose of the prior art, using as fluid a substance having the same density and physical properties of pus.
Figure 10A:
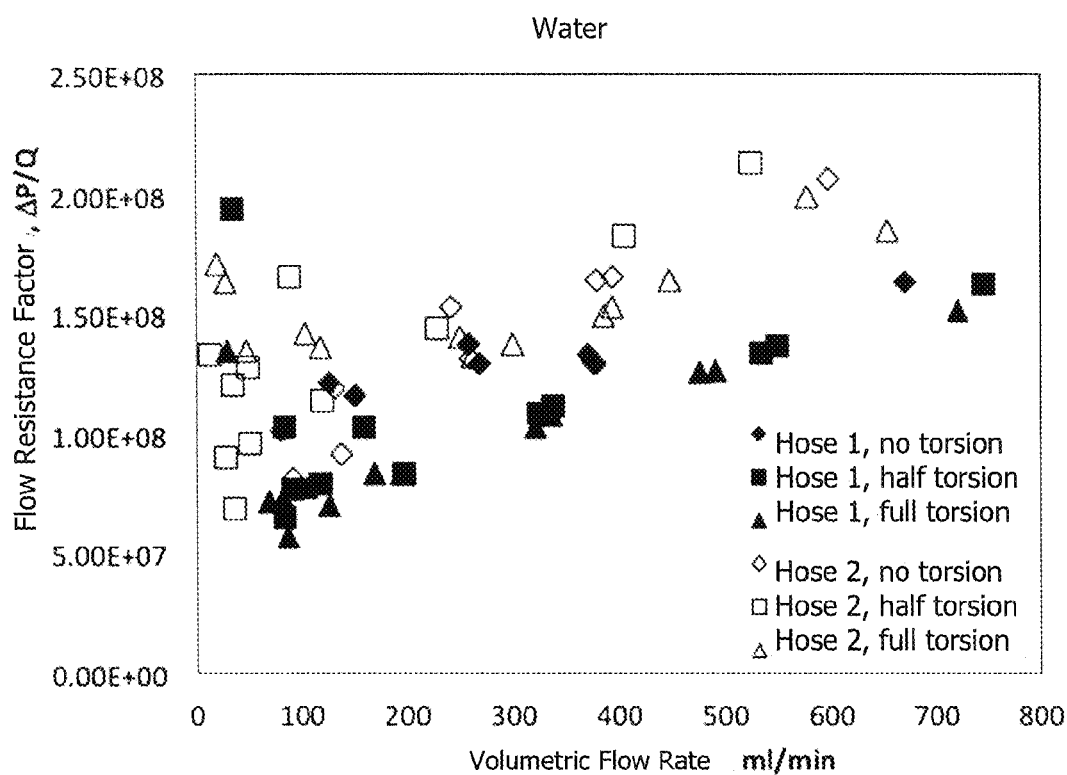
FIG. 10A is a chart of the fluid resistance factor of the drainage hose of the present invention and a hose of the prior art, using water as a fluid.
Figure 10B:
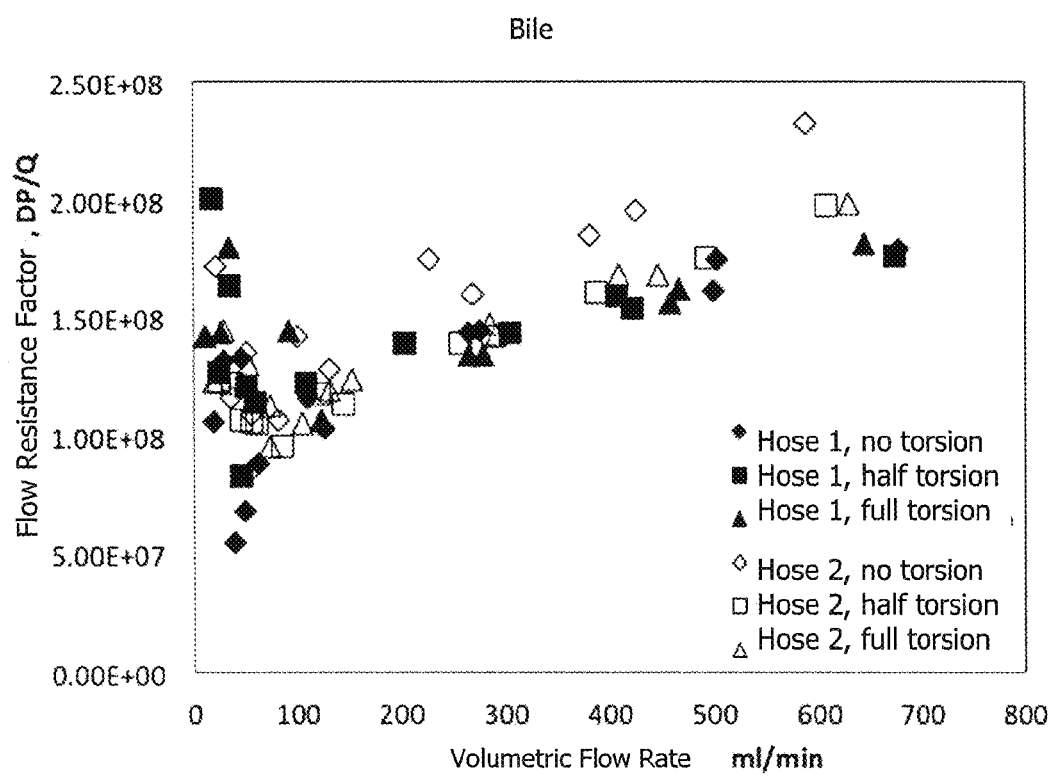
FIG. 10B is a chart of the fluid resistance factor of the drainage hose of the present invention and a hose of the prior art, using as fluid a substance having the same density and physical properties of bile.
Figure 10C:
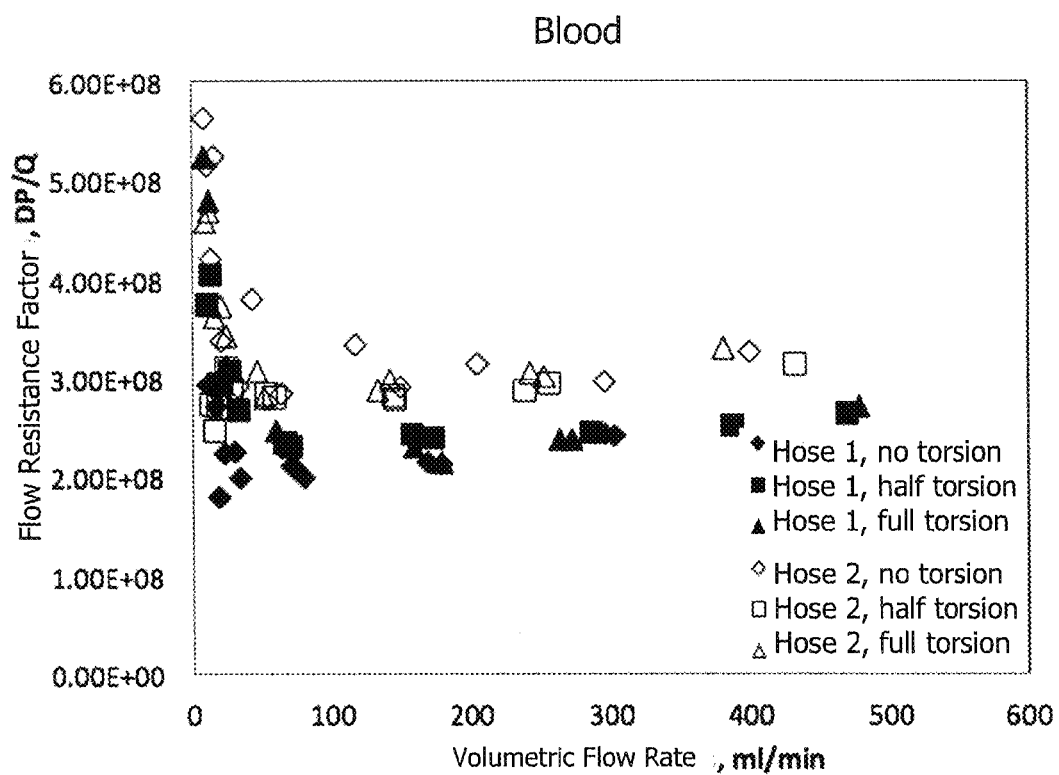
FIG. 10C is a chart of the fluid resistance factor of the drainage hose of the present invention and a hose of the prior art, using as fluid a substance having the same density and physical properties of blood.
Figure 10D:
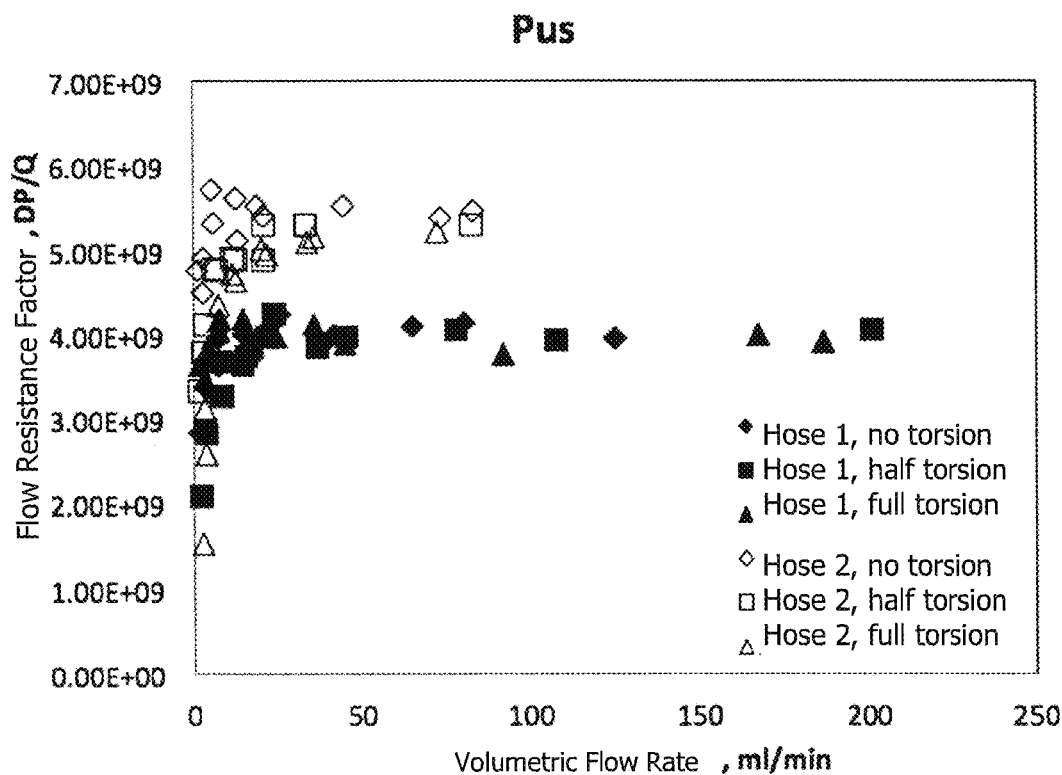
FIG. 10D is a chart of the fluid resistance factor of the drainage hose of the present invention and a hose of the prior art, using as fluid a substance having the same density and physical properties of pus.

This type of analysis was performed in order to learn how drainage hose stain behaves, as shown in FIGS. 8A and 8B. For the structural analysis, considered was the vacuum pressure generated by the peripheral equipment known as Pleurovac, which only allows exert a maximum pressure of 2000 Pa as negative pressure; the mechanical properties of the silicone with the specific feature of the hardness 50 Shore A, which hardness is recommended to be soft enough for preventing lacerate organs or tissues due to the intrusion of an element with higher hardness, and rigid enough for not occluding its own light. The simulations were performed under the same conditions of the fluid simulations. Moreover, each of the following simulations was performed using the same mesh criteria as the first analysis in which there were also performed convergence approaches.

The results obtained in FIGS. 8A and 8B indicate that, for the analysis of pressure applied, the drainage hose of the prior art suffered a maximum displacement of $4.113 \times 10^{-6}$ m, while the design of the present invention reached a maximum displacement of $9.627 \times 10^{-7}$ m. That is, the amount of displacement is reduced because the configuration of embodiments of the drainage hose optimizes the distribution of the load, in comparison to the design of the Blake hose.

Analysis 3: Performance hydrodynamic

This type of analysis was carried out to ascertain the behavior of fluids running through the drainage hose. For the performance analysis, an experimental device was used for imposing a defined pressure gradient on the two ends of the drainage hose in a controlled manner.

During the experiment, considered were three different types of fluids, as well as blood, which is a non-newtonian fluid:

| Emulated fluid | Water-Glycerin ratio (v/v) | Density (kg/m$^3$) | Viscosity (mPa s) |
|---|---|---|---|
| Water | 100-0 | 1000 | 1.0 |
| Bile | 92-8 | 1015 | 2.2 |
| Blood | 66-34 | 1084 | 3.9 |
| Pus | 20-80 | 1206 | 58.8 |

Also, two drainage hoses were used: the drainage hose illustrated in FIG. 6A, and the Blake drainage hose bigger than those illustrated in FIGS. 5A to 5D:

| Type | French size | Inner diameter (mm) | Outer diameter (mm) | Drainage hose length (mm) | Total length (mm) |
|---|---|---|---|---|---|
| Three-lobe drainage hose (1) | 24 | 5.8 | 8 | 30.5 | 1000.0 |
| Blake (2) | 24 | 5.8 | 8 | 30.5 | 1000.0 |

Moreover, three torsion conditions were considered in the hoses:
without torsion
half round torsion
full round torsion The experiment results are shown in FIGS. 9A to 9D. As can be seen, for the four cases of fluids, the three-lobe drainage hose of the present invention has a higher flow rate (ml/min) than the known drainage hose.

Moreover, with the data shown in FIGS. 9A to 9D the flow resistance factor can be measured, where that factor is obtained from the division between the pressure difference and the volume flow. The results of these calculations are presented in graphical form in FIGS. 10A to 10D. In these figures, it can be observed again that the flow rate is higher for the known drainage hose.

Figure 11:
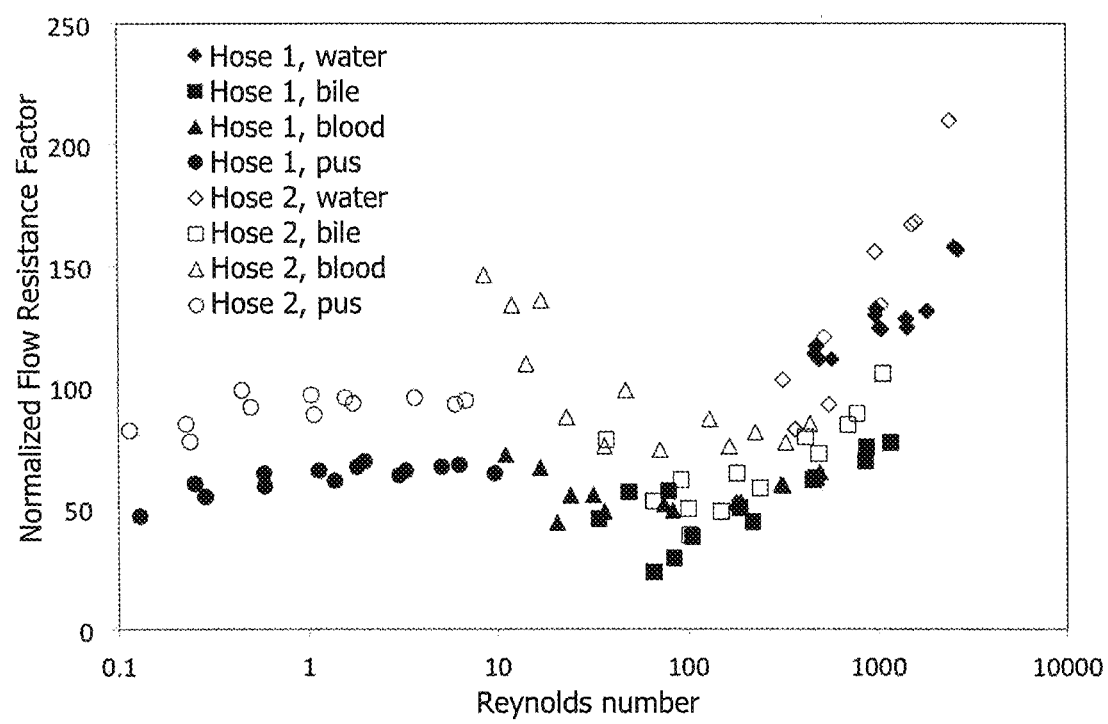
FIG. 11 is a chart of the Reynolds number versus the normalized flow resistance factor for the four fluids analyzed in the condition without torsion.

Finally, FIG. 11 illustrates the Reynolds number calculated for the case without torsion condition which takes into account the four fluids used in the experiment. In this chart it can be noted that the fluids that run through the drainage hose of the present invention have a behavior which is less turbulent (or more laminar) than the behavior of the known Blake hose, as the Reynolds number is lower under the same conditions.

Considering these results, it can be noted that the hydrodynamic performance of the drainage hose of embodiments of the present invention is better than the known hose of the prior art. In most cases, the flow resistance factor is significantly lower in the drainage hose of the present invention. Moreover, it was observed that the drainage hose of the present invention was not affected significantly by the torsion effect.

Now then, due to the fact that the circumferential curved walls (45a, 46a), (45b, 46b), (45c, 46c) outline a substantially circular outer surface, the drainage hose (40) facilitates the insertion and removal activities of the drainage hose (40) from the patient. Furthermore, the edges and rounded corners prevent unnecessary damage to the patient, as well as the formation of deposition of the drained fluid in the system.

The described elements of the drainage system (10) can be manufactured in any medical grade suitable material, including known materials or medical grade materials to be developed in the future. Preferably, the material of the described elements of the drainage system (10) is a thermosetting material. More preferably, the material of the elements of the drainage system (10) is medical grade silicone, with hardness between about 50-70 Shore A. However, it can be use any other medical grade material, for example thermoplastic materials such as polyurethane or PVC, with any hardness.

Also, in illustrative embodiments, the coupling (30) can have a greater hardness than the drainage tube (20) and the drainage hose (40), because such element is usually left between layers of skin supporting higher pressure.

The terms and expressions used throughout this disclosure are used as terms of description and not of limitation, and are not intended to exclude equivalents of the features shown and described. This application is intended to cover any adaptations or variations of embodiments of the present invention. Numerous modifications and variations will become apparent to those skilled in the art after studying the disclosure, including the use of functional substitutions and/or structural equivalents for elements described herein. All such similar variations apparent to those skilled in the art are considered within the scope of the invention as defined in the claims below.

The invention claimed is:
1. A drainage system comprising:
a drainage tube, the drainage tube defining an inner passage and terminating in a first drainage end and a second drainage end;
a tubular coupling having a first thickness that runs throughout the coupling forming a passage and a stop determined by a second thickness, the tubular coupling terminating in a first tubular coupling end and a second tubular coupling end and being substantially cylindrical; and
a drainage hose formed by a profile having an outer circumferential surface that runs along a length of the drainage hose, the drainage hose terminating in a first drainage end and a second drainage end, wherein the profile of the drainage hose comprises three symmetrical lobes, the lobes being defined by three dividing radial channels, each radial channel being in fluid communication with the outer circumferential surface through a radial channel slot along the length of the drainage hose, each radial channel extending inwardly and ending at a center of the hose and the lobes meeting at the center of the hose; wherein each of the lobes comprises:
two straight walls, each straight wall extending parallel to the radial channel beside and each straight wall having an inner side and an outer side, and two circumferential curved walls extending in opposite directions at the periphery of the hose, each straight wall is connected to a circumferential curved wall having a space formed therebetween creating a lobular lumen channel slot along the length of the drainage hose; and
wherein the inner side of the straight walls and the circumferential curved walls define a lobular lumen channel in each lobe, each lobular lumen channel being in fluid communication with the outer circum- ferential surface through the lobular lumen channel slot wherein the outer side of straight walls define the dividing radial channels between the lobes; and wherein a width of each of the radial channel slots perpendicular to the length of the drainage hose is longer than a width of each of the lobular lumen channel slots perpendicular to the length of the drainage hose.

2. The drainage system of claim 1, wherein the drainage tube has a constant outer and inner diameter that conform a tube thickness.

3. The drainage system of claim 1, wherein the drainage tube has a radiopaque line extending longitudinally in the drainage tube.

4. The drainage system of claim 1, wherein the first thickness of the coupling is less than the second thickness of the coupling, and the stop is located in the longitudinal middle of the coupling.

5. The drainage system of claim 1, wherein in each of the two ends of the coupling has an outer reduction of material in the first thickness, which forms a curving or bevel.

6. The drainage system of claim 1, wherein the angular distance of the two straight walls is 120 degrees, in each lobe.

7. The drainage system of claim 1, wherein the drainage hose has a radiopaque line extending longitudinally in the drainage hose.

8. The drainage system of claim 1, wherein the drainage tube is inserted into one end of the coupling along a first region of the passage running along the first thickness until the end of the drainage tube abuts the stop, and the drainage hose is inserted into the other end of the coupling along a second region of the passage running along the first thickness until the end of the drainage hose abuts the stop.

9. The drainage system of claim 8, wherein the passages of the drainage tube and the coupling are in fluid communication with the dividing radial channels and lobular lumen channels.

10. The drainage system of claim 1, wherein the drainage hose has a flow area per cross-section area ratio that corresponds to approximately between 39% and 42% of the area of the outer diameter that circumscribes the cross-section of the drainage hose.

11. The drainage system of claim 1, wherein the circumferential curved walls outline a substantially circular outer surface.

12. The drainage system of claim 1, wherein the coupling has a hardness greater than the hardness of the drainage tube and of the drainage hose.

13. A drain, comprising: a drainage hose formed by a profile having an outer circumferential surface that runs along a length of the drainage hose, the drainage hose terminating in a first drainage end and a second drainage end, wherein the profile of the drainage hose comprises three symmetrical lobes, the lobes being defined by three dividing radial channels, each radial channel having an end in fluid communication with the outer circumferential surface through a radial channel slot along the length of the drainage hose, each radial channel extending inwardly and ending at a center of the hose and the lobes meeting at the center of the hose; wherein each of the lobes comprises:

two straight walls, each straight wall extending parallel to the radial channel beside and each straight wall having an inner side and an outer side, and two circumferential curved walls extending in opposite directions at the periphery of the hose, each straight wall is connected to a circumferential curved wall having a space formed therebetween creating a lobular lumen channel slot along the length of the drainage hose; and wherein the inner side of the straight walls and the circumferential curved walls define a lobular lumen channel in each lobe, each lobular lumen channel being in fluid communication with the outer circumferential surface through the lobular lumen channel slot wherein the outer side of straight walls define the dividing radial channels between the lobes; and wherein a width of each of the radial channel slots perpendicular to the length of the drainage hose is longer than a width of each of the lobular lumen channel slots perpendicular to the length of the drainage hose.

14. The drainage hose of claim 13, wherein the angular distance of the two straight walls is 120 degrees, in each lobe.

15. The drainage hose of claim 13, wherein the drainage hose has a radiopaque line extending longitudinally in the drainage hose.

16. The drainage hose of claim 13, wherein the dividing radial channels and the lobular lumen channels are in fluid communication with passages of a drainage system.

17. The drainage hose of claim 13, wherein the flow area per cross-section area ratio corresponds to approximately between 39% and 42% of the area of the outer diameter that circumscribes the cross-section of the drainage hose.

18. The drainage hose of claim 13, wherein the circumferential curved walls outline a substantially circular outer surface.

* * * * *